United States Patent
Hayashi et al.

(10) Patent No.: US 8,591,712 B2
(45) Date of Patent: Nov. 26, 2013

(54) GAS SENSOR ELEMENT AND GAS SENSOR

(75) Inventors: Hiroyuki Hayashi, Konan (JP); Masaki Mizutani, Niwa-gun (JP); Takayuki Kitou, Komaki (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 13/406,188

(22) Filed: Feb. 27, 2012

(65) Prior Publication Data

US 2012/0217160 A1   Aug. 30, 2012

(30) Foreign Application Priority Data

Feb. 28, 2011 (JP) ................. 2011-041209

(51) Int. Cl.
*G01N 27/407* (2006.01)
(52) U.S. Cl.
USPC ......... 204/424; 204/426; 73/23.31; 73/23.32; 205/783.5
(58) Field of Classification Search
USPC ............... 204/421–429; 205/781, 783.5–785, 205/787; 73/23.31, 23.32
See application file for complete search history.

(56) References Cited

U.S. PATENT DOCUMENTS

| 2010/0006433 A1* | 1/2010 | Yasuda et al. | 204/424 |
| 2011/0100815 A1* | 5/2011 | Mori | 204/426 |

FOREIGN PATENT DOCUMENTS

JP   2010-38904 A   2/2010

* cited by examiner

*Primary Examiner* — J. Christopher Ball
*Assistant Examiner* — Jennifer Dieterle
(74) *Attorney, Agent, or Firm* — Sughrue Mion, PLLC

(57) ABSTRACT

There is provided a gas sensor element, including a solid electrolyte layer, a pair of sensor electrodes arranged on a front side of the solid electrolyte layer, a pair of sensor leads arranged on a rear side of the solid electrolyte layer and connected to the respective sensor electrodes; and insulating layers, one of which is arranged between one of the sensor leads and the solid electrolyte layer and the other of which is arranged between the other sensor lead and the solid electrolyte layer. The sensor electrodes have rear end portions located on the insulating layers and overlapping front end portions of the sensor leads, respectively. The sensor leads are denser than the sensor electrodes and have front ends located in the same positions as or positions rear of front ends of the insulating layers, respectively. There is also provided a gas sensor with such a gas sensor element.

3 Claims, 5 Drawing Sheets

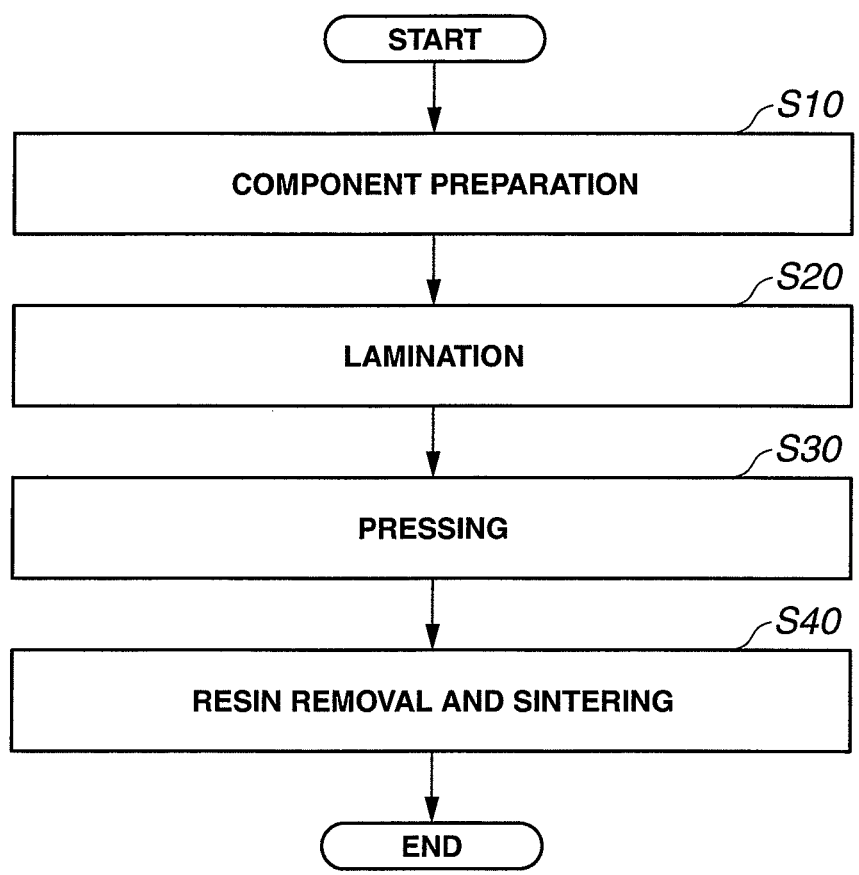

GAS SENSOR ELEMENT AND GAS SENSOR

BACKGROUND OF THE INVENTION

The present invention relates to a gas sensor element and a gas sensor having the gas sensor element.

Hereinafter, the terms "front" and "rear" are used with respect to the axial direction of a gas sensor or the longitudinal direction of a solid electrolyte layer of the gas sensor for purposes of description. These terms are illustrative and are not intended to limit the scope of the present invention.

There has been used a gas sensor for combustion control of an internal combustion engine. The gas sensor includes a sensor element capable of outputting a detection signal responsive to the concentration of a specific gas component in gas under measurement, that is, exhaust gas flowing through an exhaust pipe of the internal combustion engine. Japanese Laid-Open Patent Publication No. 2010-38904 discloses one such type of sensor element that has a plate-shaped solid electrolyte layer formed predominantly of zirconia, a pair of electrodes arranged on a front side of the solid electrolyte layer, insulating layers formed on a rear side of the solid electrolyte layer and a pair of leads arranged on the insulating layers and connected to the electrodes, respectively, so as to generate a detection signal responsive to the concentration of the specific gas component (e.g. oxygen) in the exhaust gas in accordance with a potential difference developed between the electrodes by the exhaust gas and reference gas (air) and output the detection signal to an external control device. In this gas sensor element, it is necessary that each of the electrodes have a porous structure so as to take in and allow diffusion of the exhaust gas; whereas it is preferable that each of the leads has a dense structure so as to show low electrical resistance for use in signal transmission between the electrodes and the external control device.

SUMMARY OF THE INVENTION

In the above conventional type of sensor element, front end portions of the leads and rear end portions of the electrodes overlap each other on the solid electrolyte layer in order to improve the reliability of electrical connection between the electrodes and the leads. Namely, the front end portions of the leads are located on the solid electrolyte layer directly or via the electrodes. (The portion of the solid electrolyte layer corresponding in position to the overlaps between the front end portions of the leads and the rear end portion of the electrodes is referred to as "overlap portion".) When electric current is fed between the electrodes through the leads, electric current also flows between the front end portions of the leads (or between the rear end portions of the electrodes) through the overlap portion of the solid electrolyte layer. However, in the case where the rear end portions of the electrodes overlap and cover the front end portions of the leads, the exhaust gas is taken into the rear end portions of the electrodes but is unlikely to reach the overlap portion due to the presence of the dense leads between the electrodes and the overlap portion. In the case where the front end portions of the leads overlap and cover the rear end portions of the electrodes, the exhaust gas is not taken into the rear end portions of the electrodes due to the presence of the dense leads and thereby is unlikely to reach the overlap portion. That is, the exhaust gas is unlikely to reach the overlap portion in the both cases. The dissociated ions of the specific gas component (e.g. oxygen ions) are thus hardly transferred in the overlap portion. This phenomenon tends to make the sensor element (the solid electrolyte layer) brittle and to cause the occurrence of cracks in the sensor element. As a result, the detection accuracy of the gas sensor may deteriorate.

The above problem is not limited to the above-exemplified oxygen sensor element, but is common to all of gas sensor elements where the rear end portions of the electrodes and the front end portions of the leads overlap each other on the solid electrolyte layer.

It is therefore an object of the present invention to provide a gas sensor element with electrodes and leads denser than the electrodes so as to limit the occurrence of cracks in the gas sensor element and secure the detection accuracy of the gas sensor element. It is also an object of the present invention to provide a gas sensor using the gas sensor element.

According to one aspect of the present invention, there is provided a gas sensor element for detecting the concentration of a specific gas component in gas under measurement, comprising: a plate-shaped solid electrolyte layer extending in a longitudinal direction thereof; a pair of sensor electrodes arranged on a front side of the solid electrolyte layer; a pair of sensor leads arranged on a rear side of the solid electrolyte layer and electrically connected to the respective sensor electrode; and insulating layers, one of which is arranged between one of the sensor leads and the solid electrolyte layer and the other of which is arranged between the other sensor lead and the solid electrolyte layer, wherein the sensor electrodes have rear end portions located on the insulating layers and over-lapping front end portions of the sensor leads, respectively, and wherein the sensor leads are denser than the sensor electrodes and have front ends located in the same positions as or positions rear of front ends of the insulating layers, respectively.

In the gas sensor element, the rear end portions of the sensor electrodes may preferably be located over the front end portions of the sensor leads.

According to another aspect of the present invention, there is provided a gas sensor, comprising: the above gas sensor element; and a housing retaining therein the gas sensor element.

It should be noted that the present invention can be embodied in various forms such as not only a gas sensor element and a gas sensor as mentioned above but also a method of manufacturing a gas sensor element or a gas sensor, a vehicle in which a gas sensor is mounted on a passage of gas under measurement.

The other objects and features of the present invention will also become understood from the following description.

BRIEF DESCRIPTION OF THE DRAWINGS

FIG. 4 is a schematic view showing one example of production process of the gas sensor element according to the first embodiment of the present invention.

DESCRIPTION OF THE EMBODIMENTS

Figure 1:
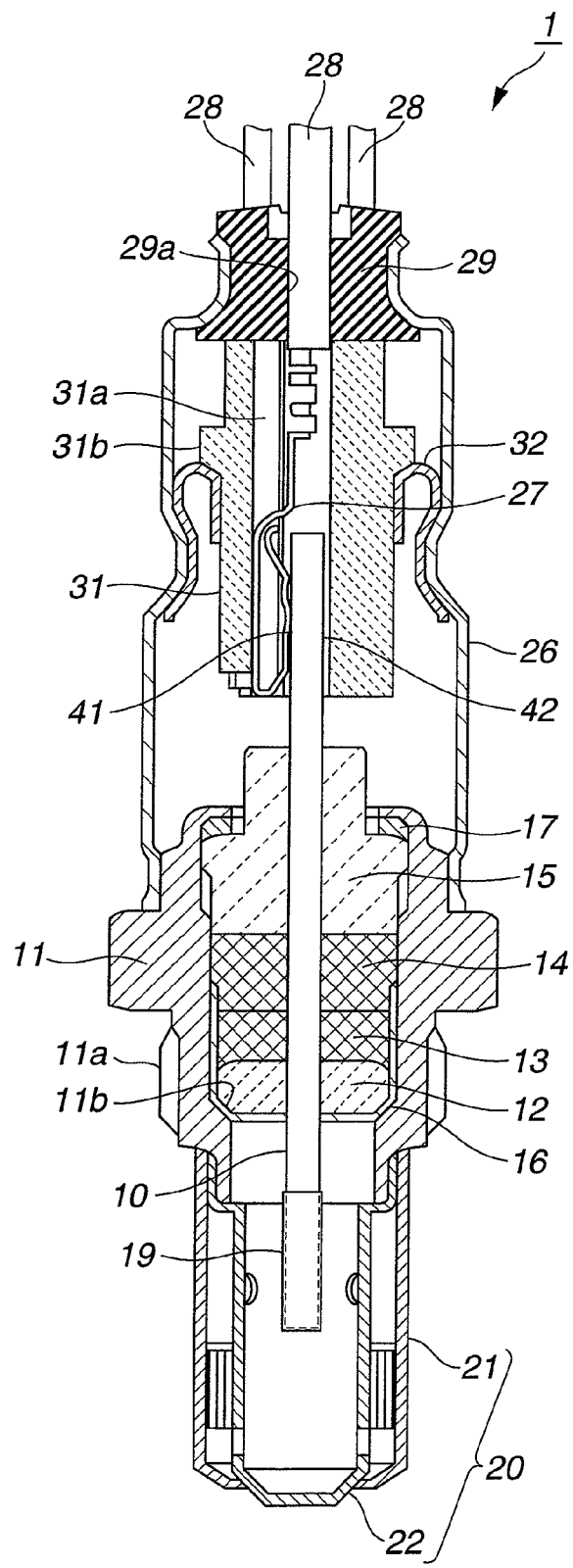
FIG. 1 is a section view of a gas sensor with a gas sensor element according to a first embodiment of the present invention.

The present invention will be described in detail below by way of the following embodiments, in which like parts and portions are designated by like reference numerals to omit repeated explanations thereof.

First Embodiment

A gas sensor 1 according to the first embodiment of the present invention is in the form of a full-range air-fuel ratio sensor mounted on an exhaust pipe of an internal combustion engine for air-fuel ratio feedback control of the internal combustion engine. Herein, the front and rear sides with respect to an axial direction of the gas sensor 1 correspond to the bottom and top sides in FIG. 1, respectively.

As shown in FIG. 1, the gas sensor 1 includes a plate-shaped sensor element 10 extending in the axial direction, a cylindrical metal shell (as a housing) 11 retaining therein the sensor element 10, with front and rear end portions of the sensor element 10 protruding from front and rear ends of the metal shell 11, respectively, and a porous protection layer 19 formed on the front end portion of the sensor element 10.

The sensor element 10 is adapted to output, to an external control device, a detection signal responsive to the concentration of a specific gas component e.g. oxygen in gas under measurement, that is, exhaust gas flowing through the exhaust pipe of the internal combustion engine as will be explained in detail later. In the first embodiment, the front end portion of the sensor element 10 protruding from the front end of the metal shell 11 and covered by the porous protection layer 19 substantially serves as a gas sensing region.

The metal shell 11 is arranged around the sensor element 10 and has a thread portion 11a formed on a radially outer side thereof so as to fix the gas sensor 1 to the exhaust pipe and a step portion 11b formed on a radially inner side thereof so as to define a taper surface inclined relative to a plane perpendicular to the axial direction.

The gas sensor 1 further includes an annular ceramic holder 12, powder filling layers 13 and 14 (also referred to as "talc rings"), a ceramic sleeve 15, a metal holder 16, a packing 17, a protector 20, an outer tube 26, a grommet 29, a cylindrical insulating contact member 31 and a retaining member 32 as shown in FIG. 1.

The metal holder 16 is retained in the metal shell 11 by the step portion 11b so as to hold therein the sensor element 10. The ceramic holder 12 and the talc rings 13 and 14 are disposed in the metal shell 11, in order of mention from the front side, so as to surround the sensor element 10. The ceramic holder 12 and the talc ring 13 are arranged in the metal holder 16. The talc ring 13 is compressed into the metal holder 16 so that the front end of the metal shell 11 is sealed with the ceramic holder 12. The ceramic sleeve 15 is arranged on a rear side of the talc ring 14 within the metal shell 11 so as to surround the sensor element 10. Further, the packing 17 is arranged on a stepped rear end portion of the ceramic sleeve 15. The rear end of the metal shell 11 is crimped to push the ceramic sleeve 15 toward the front through the packing 17 and thereby sealed with the ceramic sleeve 15 and the packing 17.

The protector 20 is formed of metal, such as stainless steel, with a plurality of gas holes and is joined by e.g. welding to the front end of the metal shell 11 so as to surround the front end portion of the sensor element 10. In the first embodiment, the protector 20 has a double structure consisting of a cylindrical outer protector member 21 and a cylindrical inner protector member 22. When the front end part of the gas sensor 1 (including the protector 20) is exposed to the exhaust gas, the exhaust gas is introduced into the inside of the protector 20 through the gas holes and fed to the front end portion (gas sensing region) of the sensor element 10 so that the sensor element 10 performs its gas concentration detection operations to output the detection signal.

The outer tube 26 is arranged around the rear end portion of the sensor element 10 and fixed to the rear end of the metal shell 11.

The insulating contact member 31 is arranged in a rear end portion of the outer tube 26 and has a protruding portion 31b formed on a radially outer side thereof and an insertion hole 31a formed therethrough in the axial direction so as to surround the rear end portion of the sensor element 10. Connection terminals 27 are provided in the insertion hole 31a and pressed against and connected to terminals 41 and 42 of the sensor element 10.

The retaining member 32 is arranged in a gap between the insulating contact member 31 and the outer tube 26 so as to retain the insulating contact member 31 in the outer tube 26 by engagement of the protruding portion 31b of the insulating contact member 31 on the retaining member 32.

The grommet 29 is fitted in a rear open end of the outer tube 26 so that the rear open end of the outer tube 26 is closed with the grommet 29. Herein, five through holes 29a are formed through the grommet 29; and five lead wires 28 are inserted through the respective through holes 29a and partly situated inside the gas sensor 1. (For purposes of clarity, only one through hole 29a and only three lead wires 28 are indicated in FIG. 1.) Each of the lead wires 28 has a front end connected to the connection terminal 27 and a rear end connected to the external control device for electrical connection between the gas sensor 1 and the external control device.

Figure 2:
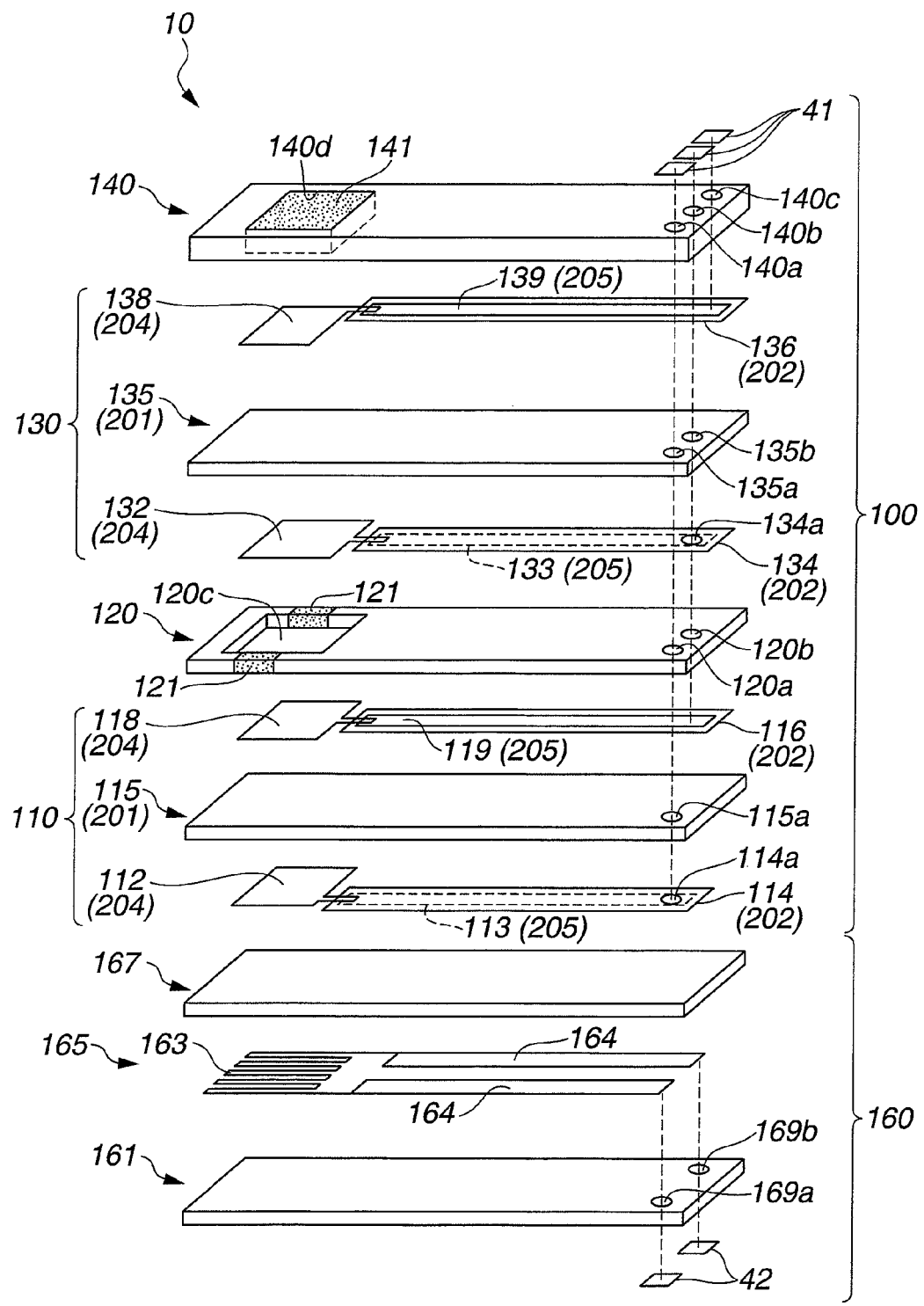
FIG. 2 is an exploded perspective view of the gas sensor element according to the first embodiment of the present invention.

As shown in FIG. 2, the sensor element 10 has a plate-shaped sensing unit 100 and a plate-shaped heating unit (heater) 160. Herein, the front and rear sides with respect to the axial direction correspond to the left and right sides in FIG. 2, respectively. (For purposes of clarity, the protection layer 19 is omitted from FIG. 2.)

Both of the sensing unit 100 and the heating unit 160 extend in the axial direction of the gas sensor 1 and laminated together into one assembly.

The sensing unit 100 has an oxygen concentration detection cell 110, an interlayer adjusting layer 120, an oxygen pumping cell 130 and a surface protection layer 140 laminated together in order of mention. A detection chamber 120c is defined in the interlayer adjusting layer 120. The terminals 41 (also referred to as "sensing-unit-side terminals") are arranged on a surface of the protection layer 140 opposite from the oxygen pumping cell 130.

The oxygen concentration detection cell 110 has a plate-shaped first solid electrolyte layer 115 arranged in such a manner that a longitudinal direction of the first solid electrolyte layer 115 is in agreement with the axial direction of the gas sensor 1, a pair of first and second electrodes 112 and 118 sandwiching therebetween the first solid electrolyte layer 115, a pair of first and second leads 113 and 119 connected to the first and second electrodes 112 and 118, respectively, and extending in the longitudinal direction of the first solid electrolyte layer 115, a first insulating layer 114 arranged between the first solid electrolyte layer 115 and the first lead 113 and a second insulating layer 116 arranged between the first solid electrolyte layer 115 and the second lead 119. In the oxygen concentration detection cell 110, the first electrode 112 serves as an oxygen reference electrode (also referred to as "reference oxygen chamber") in which the oxygen concentration of the reference oxygen chamber is kept at a constant level by the passage of a constant current between the first and second electrodes 112 and 118.

The first electrode 112 is formed into e.g. a substantially rectangular shape and located on a front side of one main surface (lower side in FIG. 2) of the first solid electrolyte layer 115. The first electrode 112 has a certain degree of porosity (pores) so as to take in and be filled with oxygen.

The first lead 113 is located on a rear side of the one main surface of the first solid electrolyte layer 115 and is electrically connected at a front end portion thereof to a rear end portion of the first electrode 112.

In the first embodiment, the first lead 113 is made denser than the first electrode 112. In other words, the first lead 113 has a lower porosity (higher density) than that of the first electrode 112. In still other words, the amount of gas permeation per unit volume of the first lead 113 is smaller than that of the first electrode 112. It is known that, in the case where conductor members are formed of the same material or similar materials, the denser one of the conductor members generally shows lower electrical resistance than that of the other conductor member. As the first lead 113 is made denser than the first electrode 112 in the first embodiment, the first lead 113 shows lower electrical resistance and enables good signal transmission as compared to the case where the first lead 113 is as dense as the first electrode 112.

The first insulating layer 114 is formed directly on the rear side of the one main surface of the first solid electrolyte layer 115 so as to extend in the longitudinal direction of the first solid electrolyte layer 115. Namely, the first lead 113 is formed on the first solid electrolyte layer 115 so as to sandwich the first insulating layer 114 between the first lead 113 and the first solid electrolyte layer 115 in the first embodiment. As the first insulating layer 114 is arranged between the first solid electrolyte layer 115 and the first lead 113, the first solid electrolyte layer 115 and the first lead 113 are kept insulated from each other by the first insulating layer 114.

A first through hole 114a, a second through hole 115a, a third through hole 120a, a sixth through hole 135a and an eighth through hole 140a are formed through the first insulating layer 114, the first solid electrolyte layer 115, the interlayer adjusting layer 120, the second solid electrolyte layer 135 and the surface protection layer 140, respectively, so that the first lead 113 is electrically connected at a rear end portion thereof to one of the sensing-unit-side terminals 41 via the through holes 114a, 115a, 120a, 135a and 140a.

The second electrode 118 is formed into e.g. a substantially rectangular shape and located on a front side of the other main surface (upper side in FIG. 2) of the first solid electrolyte layer 115. The second electrode 118 has a certain degree of porosity (pores) so as to allow diffusion (flow) of the exhaust gas from the outside.

The second lead 119 is located on a rear side of the other main surface of the first solid electrolyte layer 115 and is electrically connected at a front end portion thereof to a rear end portion of the second electrode 118.

In the first embodiment, the second lead 119 is made denser than the second electrode 118 as in the case of the first lead 113. In other words, the second lead 119 has a lower porosity (higher density) than that of the second electrode 118. In still other words, the amount of gas permeation per unit volume of the second lead 119 is smaller than that of the second electrode. As the second lead 119 is made denser than the second electrode 118 in the first embodiment, the second lead 119 shows lower electrical resistance and enables good signal transmission as compared to the case where the second lead 119 is as dense as the second electrode 118.

The second insulating layer 116 is formed directly on the rear side of the other main surface of the first solid electrolyte layer 115 so as to extend in the longitudinal direction of the first solid electrolyte layer 115. Namely, the second lead 119 is formed on the first solid electrolyte layer 115 so as to sandwich the second insulating layer 116 between the second lead 119 and the first solid electrolyte layer 115 in the first embodiment. As the second insulating layer 116 is arranged between the first solid electrolyte layer 115 and the second lead 119, the first solid electrolyte layer 115 and the second lead 119 are kept insulated from each other by the second insulating layer 116.

A fourth through hole 120b, a fifth through hole 134a, a seventh through hole 135b and a ninth through hole 140b are formed through the interlayer adjusting layer 120, the third insulating layer 134, the second solid electrolyte layer 135 and the surface protection layer 140, respectively, so that the second lead 119 is electrically connected at a rear end portion thereof to another one of the sensing-unit-side terminals 41 via the through holes 120b, 134a, 135b and 140b.

The oxygen pumping cell 130 has a plate-shaped second solid electrolyte layer 135 arranged in such a manner that a longitudinal direction of the second solid electrolyte layer 135 is in agreement with the axial direction of the gas sensor 1, a pair of third and fourth electrodes 132 and 138 sandwiching therebetween the second solid electrolyte layer 135, a pair of third and fourth leads 133 and 139 connected to the third and fourth electrodes 132 and 138, respectively, and extending in the longitudinal direction of the second solid electrolyte layer 135, a third insulating layer 134 arranged between the second solid electrolyte layer 135 and the third lead 133 and a fourth insulating layer 136 arranged between the second solid electrolyte layer 135 and the fourth lead 139. The oxygen pumping cell 130 performs oxygen pumping action to pump oxygen in or out of the detection chamber 120c by the control of a current flow between the third and fourth electrodes 132 and 138.

The third electrode 132 is formed into e.g. a substantially rectangular shape and located on a front side of one main surface (lower side in FIG. 2) of the second solid electrolyte layer 135. The third electrode 132 has a certain degree of porosity (pores) so as to allow diffusion (flow) of the exhaust gas from the outside.

The third lead 133 is located on a rear side of the one main surface of the second solid electrolyte layer 135 and is electrically connected at a front end portion thereof to a rear end portion of the third electrode 132.

In the first embodiment, the third lead 133 is also made denser than the third electrode 132. In other words, the third lead 133 has a lower porosity (higher density) than that of the third electrode 132. In still other words, the amount of gas permeation per unit volume of the third lead 133 is smaller than that of the third electrode 132. As the third lead 133 is made denser than the third electrode 132 in the first embodiment, the third lead 133 shows lower electrical resistance and enables good signal transmission as compared to the case where the third lead 133 is as dense as the third electrode 132.

The third insulating layer 134 is formed directly on the rear side of the one main surface of the second solid electrolyte layer 135 so as to extend in the longitudinal direction of the second solid electrolyte layer 135. Namely, the third lead 133 is formed on the second solid electrolyte layer 135 so as to sandwich the third insulating layer 134 between the third lead 133 and the second solid electrolyte layer 135 in the first embodiment. As the third insulating layer 134 is arranged between the second solid electrolyte layer 135 and the third lead 133, the second solid electrolyte layer 135 and the third lead 133 are kept insulated from each other by the third insulating layer 134.

Further, the third lead 133 is electrically connected at a rear end portion thereof to the another one of the sensing-unit-side terminals 41 via the fifth through hole 134a, the seventh through hole 135b and the ninth through hole 140b. The second lead 119 and the third lead 133 are kept at the same potential via the through hole 120b.

The fourth electrode 138 is formed into e.g. a substantially rectangular shape and located on a front side of the other main surface (upper side in FIG. 2) of the second solid electrolyte layer 135. As in the case of the third electrode 132, the fourth electrode 138 has a certain degree of porosity (pores) so as to allow diffusion (flow) of the exhaust gas from the outside.

The fourth lead 139 is located on a rear side of the other main surface of the second solid electrolyte layer 135 and is electrically connected at a front end portion thereof to a rear end portion of the fourth electrode 138.

As in the case of the third lead 133, the fourth lead 139 is made denser than the fourth electrode 138 in the first embodiment. In other words, the fourth lead 139 has a lower porosity (higher density) than that of the fourth electrode 138. In still other words, the amount of gas permeation per unit volume of the fourth lead 139 is smaller than that of the fourth electrode 138. As the fourth lead 139 is made denser than the fourth electrode 138 in the first embodiment, the fourth lead 139 shows lower electrical resistance and enables good signal transmission as compared to the case where the fourth lead 139 is as dense as the fourth electrode 138.

The fourth insulating layer 136 is formed directly on the rear side of the other main surface of the second solid electrolyte layer 135 so as to extend in the longitudinal direction of the second solid electrolyte layer 135. Namely, the fourth lead 139 is formed on the second solid electrolyte layer 135 so as to sandwich the fourth insulating layer 136 between the fourth lead 139 and the second solid electrolyte layer 135 in the first embodiment. As the fourth insulating layer 136 is arranged between the second solid electrolyte layer 135 and the fourth lead 139, the second solid electrolyte layer 135 and the fourth lead 139 are kept insulated from each other by the fourth insulating layer 136.

A tenth through hole 140c is formed through the surface protection layer 140 so that the fourth lead 139 is electrically connected at a rear end portion thereof to the remaining one of the sensing-unit-side terminals 41 via the through hole 140c.

In the first embodiment, the structural density (hermeticity) of the first to fourth electrodes 112, 118, 132 and 138 are set to the same level; and the structural density (hermeticity) of the first to fourth leads 113, 119, 133 and 139 are set to the same level.

The interlayer adjusting layer 120 is laminated between the oxygen concentration detection cell 110 and the oxygen pumping cell 130 as mentioned above. In the interlayer adjusting layer 120, the detection chamber 120c is defined at a position between the second and third electrodes 118 and 132. Diffusion limiting members 121 are arranged on both sides of the detection chamber 120c in a width direction of the solid electrode layer 115, 135 so that the detection chamber 120c is communication with the outside via the diffusion limiting members 121. Each of the diffusion limiting members 121 has a certain degree of porosity so as to introduce the exhaust gas into the detection chamber 120c at a constant limited rate regardless of the flow rate of the exhaust gas outside the sensor element 10.

The surface protection layer 140 is laminated on the other main surface of the second solid electrolyte layer 135 so as to sandwich the fourth electrode 138 and the fourth lead 139 between the surface protection layer 140 and the second solid electrolyte layer 135. A hole 140d is formed through a portion of the surface protection layer 140 overlapping the fourth electrode 138. An electrode protection member 141 is fitted in the hole 140d.

On the other hand, the heating unit 160 has first and second substrates 161 and 167 formed predominantly of alumina and a heating resistor 165 arranged between the first and second substrates 161 and 167. The terminals 42 (also referred to as "heating-unit-side terminals") are arranged on a surface of the first substrate 161 opposite from the heating resistor 165.

The heating resistor 165 has a heating portion 163 formed predominantly of platinum and a pair of heater leads 164 extending from the heating portion 163 in a longitudinal direction of the substrate 161, 167. Through holes 169a and 169b are formed through the first substrate 161 so that the heater leads 164 are electrically connected at ends thereof to the heater-side terminals 42 via the through holes 169a and 169b.

The normal operations (gas concentration detection operations) of the above-structured gas sensor 1 will be explained below for reference.

In the normal operations of the gas sensor 1, the heating unit 160 is energized to heat the sensing unit 100 to an activation temperature (e.g. 600° C. or higher) under the control of a heater control circuit of the external control device. Further, the first electrode 112 is actuated to serve as the oxygen reference electrode (reference oxygen chamber) by the passage of a small electric current (e.g. 15 μA) through the oxygen concentration detection cell 110 through the terminals 41. In this state, there develops a voltage of e.g. about 450 mV between the first electrode 112 (where the oxygen concentration of the reference oxygen chamber is kept at a constant level) and the second electrode 118 when the atmosphere of the gas detection chamber 120c is maintained at a theoretical air-fuel ratio. The amount and direction of flow of electric current Ip through the oxygen pumping cell 130 is thus controlled as appropriate in such a manner as to adjust the voltage Vs of the oxygen concentration detection cell 110 to about 450 mV and maintain the atmosphere of the gas detection chamber 120c at the theoretical air-fuel ratio. The gas sensor 1 outputs the current value Ip as the detection signal so that the oxygen concentration of the exhaust gas can be determined based on the current output Ip. Under the above current control, oxygen (oxygen molecules) is dissociated by each of the electrodes 112, 118, 132 and 138. The resulting oxygen ions are transferred through the solid electrolyte layer 115, 135 in a thickness direction of the solid electrolyte layer 115, 135.

Hereinafter, the first and second solid electrolyte layers 115 and 135 are generically called "solid electrolyte layers 201"; the first to fourth insulating layers 114, 116, 134 and 136 are generically called "insulating layers 202"; the first to fourth electrodes 112, 118, 132 and 138 are generically called "sensor electrodes 204"; and the first to fourth leads 113, 119, 133 and 139 are generically called "sensor leads 205".

Figure 3A:
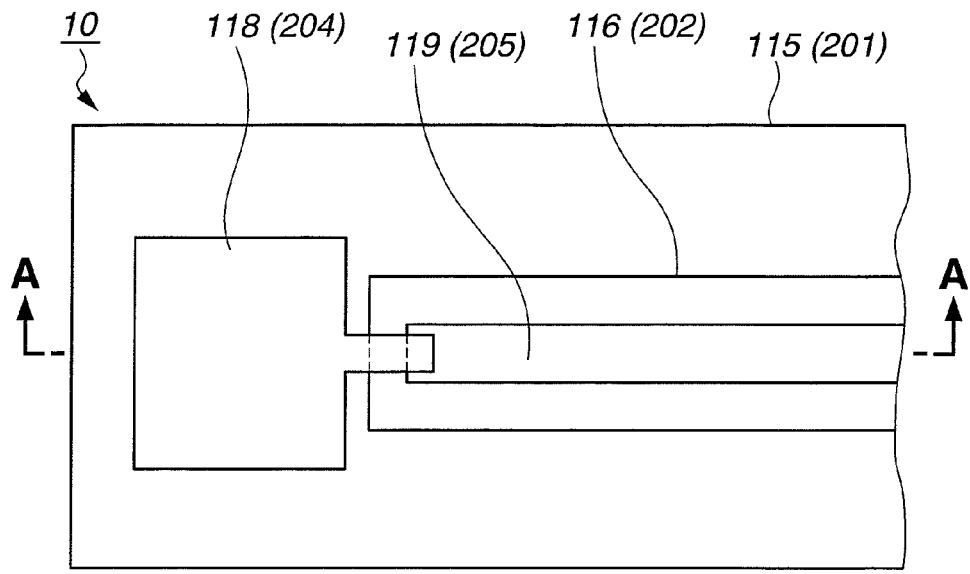
FIG. 3A is a plan view of the gas sensor element according to the first embodiment of the present invention.
Figure 3B:
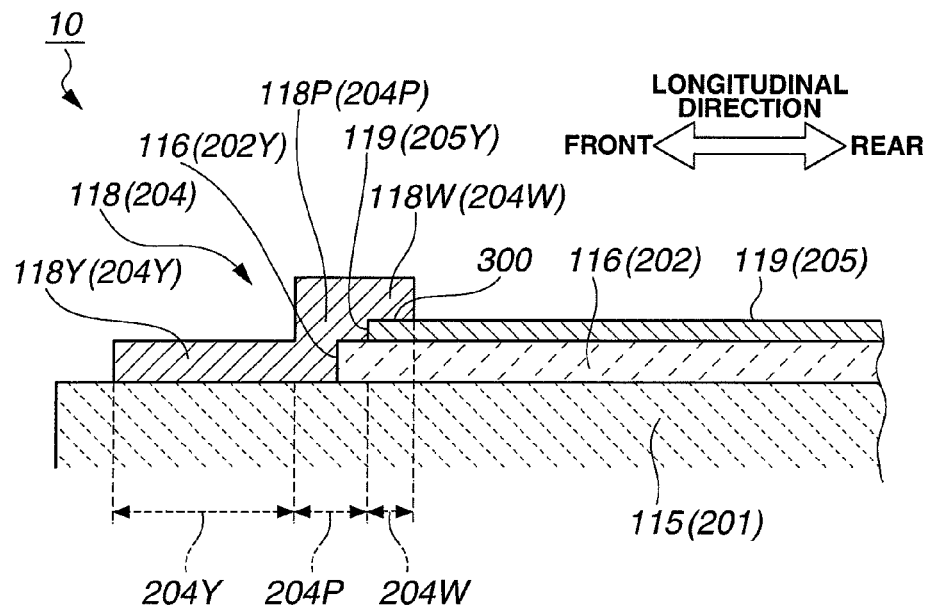
FIG. 3B is a section view of the gas sensor element taken along line A-A of FIG. 3A.
Figure 5:
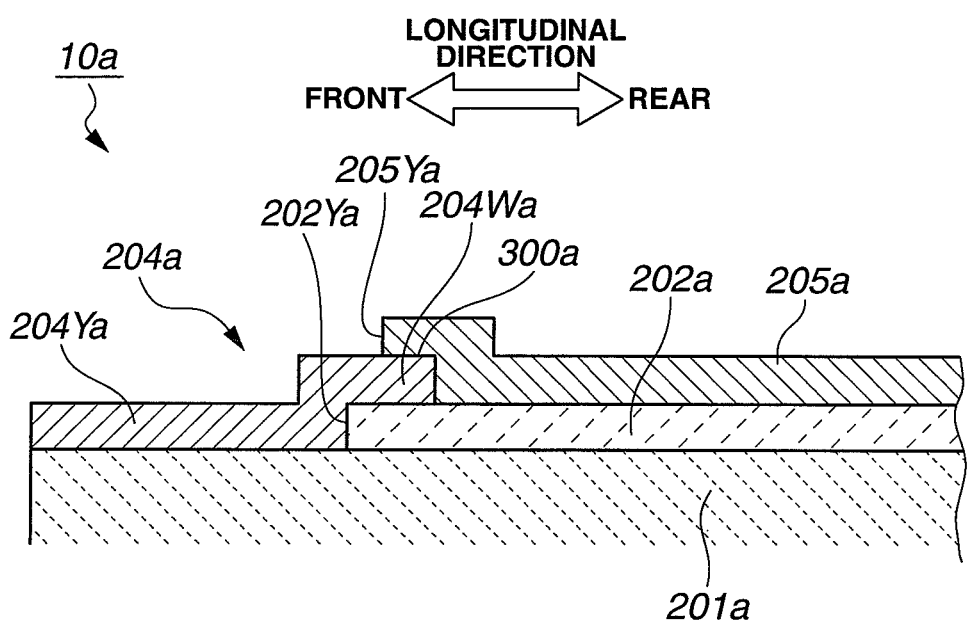
FIG. 5 is a schematic view of a gas sensor element according to a second embodiment of the present invention.

In the first embodiment, the sensor element 10 has a specific lamination structure of the insulating layer 202, the sensor electrode 204 and the sensor lead 205 on the solid electrolyte layer 201 as shown in FIGS. 3A and 3B. In FIGS. 3A and 3B, the lamination structure of the insulating layer 116, the second electrode 118 and the second lead 119 on the first solid electrolyte layer 115 is shown as a typical example.

More specifically, the insulating layer 202 is formed directly on the solid electrolyte layer 201. The sensor lead 205 is formed directly on the insulating layer 202 and is not formed directly on the solid electrolyte layer 201. Further, the sensor lead 205 has a front end 205Y located at a position rear of a front end 202Y of the insulating layer 202 in the longitudinal direction of the solid electrolyte layer 201 (horizontal direction in FIG. 2). The sensor electrode 204 has a front end portion 204Y formed directly on the solid electrolyte layer 201, a rear end portion 204W (as a connection portion) directly overlapping and covering a front end portion of the sensor lead 205 to establish an overlap portion 300 between the rear end portion 204W of the sensor electrode 204 and the sensor lead 205. An intermediate portion 204P extends between the front and rear end portions 204Y and 204W. In other words, the rear end portion 204W of the sensor electrode 204 is located on the solid electrolyte layer 201, with the insulating layer 202 and the sensor lead 205 sandwiched between the rear end portion 204W of the sensor electrode 204 and the solid electrolyte layer 201. In still other words, the front and rear end portions 204Y and 204W of the sensor electrode 204 are in direct contact with surfaces of the solid electrolyte layer 201 and the insulating layer 202, respectively; and the intermediate portion 204P of the sensor electrode 204 is raised from the solid electrolyte layer 201 to the insulating layer 202. In smallest-thickness comparison of the sensor electrode 204 and the sensor lead 205, the sensor lead 205 is smaller in thickness than the sensor electrode 204. Furthermore, the sensor lead 205 is made denser than the sensor electrode 204 as mentioned above. Although not shown in FIGS. 3A and 3B, the sensor lead 105 has a rear end located at a position front of a rear end of the insulating layer 202 in the longitudinal direction of the solid electrolyte layer 201.

In the above lamination structure, the sensor lead 205 is located on the insulating layer 202 and is not in direct contact with the solid electrolyte layer 201 in the sensor element 10. Namely, the sensor lead 205 is kept insulated from the solid electrolyte layer 201 by the insulating layer 202 so that there does not arise a current flow between the entire lengths of the sensor leads 205 through the solid electrolyte layer 201 during the passage of electric current between the sensor electrodes 204 through the sensor lead 205s. As a result, the transfer of the oxygen ions takes place in only part of the solid electrolyte layer 201 corresponding in position to the sensor electrodes 204 (except for the portions thereof located on the insulating layers 202) and does not take place in part of the solid electrolyte layer 201 corresponding in position to the sensor leads 205. This makes it possible to protect the solid electrolyte layer 201 from blackening and thereby prevent the solid electrolyte layer 201 from becoming brittle. The occurrence of cracks in the sensor element 10 can be thus prevented effectively so as not cause deterioration in the detection accuracy of the gas sensor 1. Further, the signal transmission between the sensor element 10 (sensor electrode 204) and the external control device can be done favorably as the sensor lead 205 is made dense than the sensor electrode 204 and lower in electrical resistance.

The above-mentioned sensor element 10 can be produced, as shown in FIG. 4, by forming green (unsintered) structural components (step S10), laminating the green structural components to one another (step S20), pressing the laminated green structural components together at a given pressure (step S30), and then, subjecting the laminated green structural components to resin removal (sometimes also called "binder removal") and sintering (step S40). The production procedure of the sensor element 10 will be explained in more detail below. It should be noted that, in the following explanation, each of the structural components before and after sintering is designated by the same reference numeral for convenience.

The first and second substrates 161 and 167 are provided in the green (unsintered) state as follows (step S10). A slurry is first prepared by wet-mixing a mixed powder of 97 mass % alumina powder and 3 mass % silica, a binder and a plasticizer. The prepared slurry is formed into a sheet (plate) by sheet forming process using a doctor blade device. The resulting sheet material is cut into a predetermined size and used as the unsintered substrate 161, 167. The through holes 169a and 169b are formed through the unsintered first substrate 161 at given positions.

The heating resistor 165 is provided in the green (unsintered) state by preparing a paste containing platinum as a main ingredient (step S10) and screen-printing the paste on the unsintered first substrate 161 (step S20).

The interlayer adjusting layer 120 is provided in the green (unsintered) state (step S10) by preparing the same sheet material as that of the first and second substrates 161 and 167, cutting the prepared sheet material into a predetermined size and forming the detection chamber 120c and the through holes 120a and 120b through the cut sheet material at given positions. The diffusion limiting members 121 are provided in the green (unsintered) state by wet-mixing an alumina powder, a carbon powder, a binder and a plasticizer and applying the resulting slurry to the interlayer adjusting layer 120.

The surface protection layer 140 is provided in the green (unsintered) state as follows (step S10) by preparing the same sheet material as that of the first and second substrates 161 and 167, cutting the prepared sheet material into a predetermined size and forming the through holes 140a, 140b and 140c and the hole 140d through the cut sheet material at give positions. Further, the electrode protection member 141 is provided in the green (unsintered) state by wet-mixing a mixed powder of 63 mass % alumina powder, 3 mass % silica and 34 mass % carbon powder, a binder and a plasticizer and applying the resulting slurry to the surface protection layer 140.

The solid electrolyte layer 201 is provided in the green (unsintered) state as follows (step S10). A slurry is first prepared by wet-mixing a mixed powder of 97 mass % zirconia powder and 3 mass % silica, a binder and a plasticizer. The prepared slurry is formed into a sheet (plate). The resulting sheet material is cut into a predetermined size and used as the unsintered solid electrolyte layer 201. The through holes 135a and 135b are formed through the unsintered solid electrolyte layer 201 at give positions.

The insulating layer 202 is provided in the green (unsintered) state as follows (step S10). There is first prepared a slurry containing 97 mass % alumina powder and 3 mass % silica powder assuming the total amount of the alumina powder and the silica powder as 100 mass %. There is also prepared a binder solution by mixing a binder, a plasticizer and acetone. Further, an organic solvent is prepared. An insulating-layer-forming paste is prepared by adding the binder solution and the organic solvent to the prepared slurry, and then, kneading the resulting mixture while evaporating the acetone. The prepared paste is applied, as the unsintered insulating layer 202, onto the rear side of the solid electrolyte layer 201 by e.g. screen printing.

The sensor lead 205 is provided in the green (unsintered) state as follows (step S10). A slurry is prepared from a conductive material (such as noble metal e.g. platinum, gold etc.), zirconia powder and alumina powder. In the first embodiment, platinum particles are used as the conductive material. Further, a solution of a binder, a plasticizer and acetone and an organic solvent are prepared. A lead-forming paste is prepared by adding the binder solution and the organic solvent to the prepared slurry, and then, kneading the resulting mixture while evaporating the acetone. The prepared paste is applied, as the unsintered sensor lead 205, onto the insulating layer 202 by e.g. screen printing.

The sensor electrode 204 is provided in the green (unsintered) state as follows (step S10). A slurry is prepared from a conductive material (such as noble metal e.g. platinum, gold etc.) and zirconia powder. In the first embodiment, platinum particles are used as the conductive material. Further, a solution of a binder, a plasticizer and acetone and an organic solvent are prepared. An electrode-forming paste is prepared by adding the binder solution and the organic solvent to the prepared slurry, and then, kneading the resulting mixture while evaporating the acetone. The prepared paste is applied, as the unsintered sensor electrode 204, onto the front side of the solid electrolyte layer 201 and the front end portion of the sensor lead 205 by e.g. screen printing. In this stage, the sensor electrode 204 and the sensor lead 205 are connected to each other.

In the formation of the sensor electrode 204 and the sensor lead 205, the electrode-forming paste and the lead-forming paste are screen-printed in such a manner that, after the sintering, the sensor lead 205 is smaller in thickness than the sensor electrode 204.

Further, the sensor electrode 204 and the sensor lead 205 are formed in such a manner that, after the sintering, the sensor lead 205 is denser than the sensor electrode 204. It is feasible to make the sensor lead 205 denser than the sensor electrode 204 by e.g. adjusting the amount of the binder in the lead-forming paste and the amount of the binder in the electrode-forming paste. More specifically, the amount of the binder in the lead-forming paste is set smaller than the amount of the binder in the electrode-forming paste. As the binder is burned out and removed during the sintering, the sensor lead 205 is made denser than the sensor electrode 204 under such binder amount control. It is alternatively feasible to make the sensor lead 205 denser than the sensor electrode 204 by using the conductive material of lower melting point in the lead-forming paste than that used in the electrode-forming paste. As the conductive material is molten during the sintering, the sensor lead 205 is made denser than the sensor electrode 204 by such selection of the conductive materials. It is also alternatively feasible to make the sensor lead 205 denser than the sensor electrode 204 by using the conductive material of smaller particle size, or more perfect circle particle shape, in the lead-forming paste than that used in the electrode-forming paste. Herein, the structural density (hermeticity) of the sensor electrode 204 and the structural density (hermeticity) of the sensor lead 205 can be determined by so-called "leak test" using e.g. a He leak detector ("MS-50" manufactured by Vacuum Instrument Corporation).

Further, the terminals 41 and 42 are provided in the green (unsintered) state by preparing a paste of zirconia powder and platinum powder (step S10), screen-printing and drying the prepared paste in the appropriate through holes of the corresponding substrate (step S20).

After the green (unsintered) structural components are laminated to one another (step S20), the laminated green structural components are pressed together at a given pressure (step S30), and then, subjected to resin removal and sintering (step S40). With this, the sensor element 10 is completed.

In general, it is less likely that, in the case of forming two layers by e.g. screen printing in such a manner that the two layers partly overlaps each other, cracks will occur in these two layers when the thicker one of the two layers is located over the other (thinner) layer. In the first embodiment, the sensor electrode 204 and the sensor lead 205 are electrically connected by the overlap portion 300 where the rear end portion 204W of the larger-thickness sensor electrode 204 is located over and covers the front end portion of the smaller-thickness sensor lead 205 as shown in FIG. 3B. This makes it possible to prevent the occurrence of cracks in the sensor electrode 204 and the sensor lead 205 more effectively as compared to the case where the front end portion of the smaller-thickness sensor lead 205 is located over and covers the rear end portion 204W of the larger-thickness sensor electrode 204. The electrical connection (conduction) of the sensor electrode 204 and the sensor lead 205 can be thus maintained stably. In addition, the amount of the raw material (especially, conductive material) of the sensor lead 205 can be decreased so as to reduce the production cost of the sensor element 10 as the longitudinally-extending sensor lead 205 is made smaller in thickness than the sensor electrode 204.

Second Embodiment

A sensor element 10a according to the second embodiment is structurally similar to the sensor element 10 according to the first embodiment, except that the sensor element 10a has a different lamination structure of an insulating layer 202a, a sensor electrode 204a and a sensor lead 205a on a solid electrolyte layer 201a (more specifically, a different positional/dimensional relationship of sensor electrode 204a and sensor lead 205a). The other configurations of the sensor element 10a are the same as those of the sensor element 10 and thus will not be herein explained. As in the first embodiment, the sensor element 10a is designed as a structural element of the gas sensor 1.

In the second embodiment, the sensor lead 205a is formed on the solid electrolyte layer 201a so as to sandwich the insulating layer 202a between the sensor lead 205a and the solid electrolyte layer 201a as in the first embodiment. Further, the sensor lead 205a has a front end 205Ya located at a position rear of a front end 202Ya of the insulating layer 202a and a rear end located at a position front of a rear end of the insulating layer 202a. The insulating layer 202a is thus definitely located between the solid electrolyte layer 201a and the sensor lead 205a.

The sensor electrode 204a has a front end portion 204Ya formed directly on the solid electrolyte layer 201a and a rear end portion 204Wa (as a connection portion) formed directly on the insulating layer 202a and sandwiched between the insulating layer 202a and the sensor lead 205a to establish an overlap portion 300a between the sensor electrode 204a and the sensor lead 205a.

The sensor lead 205a and the sensor electrode 204a are the same in thickness in the second embodiment.

As mentioned above, the sensor lead 205a is located on the insulating layer 202a and is not in direct contact with the solid electrolyte layer 201a. As there does not arises a current flow between the sensor leads 205a through the solid electrolyte layer 201a, the transfer of the oxygen ions does not take place in part of the solid electrolyte layer 201a corresponding in position to the sensor leads 205a as in the first embodiment. This makes it possible to protect the solid electrolyte layer 201a from blackening and prevent the solid electrolyte layer 201a from becoming brittle. The occurrence of cracks in the sensor element 10a can be thus prevented effectively so as not cause deterioration in the detection accuracy of the gas sensor 1.

The sensor element 10a can be produced as follows in the second embodiment.

The solid electrolyte layer 201a is provided in the green (unsintered) state by preparing a raw material slurry, forming the raw material slurry into a sheet and cutting the sheet material into a predetermined size. The insulating layer 202a is provided in the green (unsintered) state by preparing an insulating-layer-forming paste and screen-printing the prepared paste on the rear side of the unsintered solid electrolyte layer 201a. The sensor electrode 204a is provided in the green (unsintered) state by preparing an electrode-forming paste and screen-printing the prepared paste on the front side of the solid electrolyte layer 201a and the front end portion of the insulating layer 202a. The sensor lead 205a is provided in the green (unsintered) state by preparing a lead-forming paste and screen-printing the prepared paste on the insulating layer 202 and on the rear end portion 204Wa of the sensor electrode 204a. The thus-obtained sensing unit 100 is further laminated together with the other structural components. The resulting unsintered sensor element 10a is subjected to pressing at a given pressure, and then, subjected to resin removal and sintering.

The entire contents of Japanese Patent Application No. 2011-041209 (filed on Feb. 28, 2011) are herein incorporated by reference.

Although the present invention has been described above with reference to the specific exemplary embodiments, the present invention is not limited to the above-described exemplary embodiments. Various modifications and variations of the embodiments described above will occur to those skilled in the art in light of the above teachings. For example, the following modifications are possible.

First Modification

In the first embodiment, the sensor lead 205 is smaller in thickness than the sensor electrode 204. On the other hand, the sensor lead 205a and the sensor electrode 204a are the same in thickness in the second embodiment. The thickness relationship of the sensor electrode 204, 204a and the sensor lead 205, 205a is not however limited to the above and can be set as appropriate. As long as the sensor lead 205, 205a is formed on the insulating layer 202, 202a so as to sandwich the insulating layer 202, 202a between the sensor lead 205, 205a and the solid electrolyte layer 201, 201a, it is possible to prevent the solid electrolyte layer 201, 201a from becoming brittle due to the current flow through part of the solid electrolyte layer 201, 201a corresponding in position to the sensor leads 205, 205a and thereby possible to prevent the occurrence of cracks in the sensor element 10, 10a.

Second Modification

The front end 205Y, 205Ya of the sensor lead 205, 205a is located rear of the front end 202Y, 202Ya of the insulating layer 202, 202a in the above embodiment. However, the positional relationship of the front end 205Y, 205Ya of the sensor lead 205, 205a and the front end 202Y, 202Ya of the insulating layer 202, 202a is not limited to the above. The front end 205Y, 205Ya of the sensor lead 205, 205a may alternatively be located in the same position as the front end 202Y, 202Ya of the insulating layer 202, 202a in the longitudinal direction of the solid electrolyte layer 201, 201a. It is possible even by such a positional relationship to prevent the solid electrolyte layer 201, 201a from becoming brittle due to the current flow through part of the solid electrolyte layer 201, 201a corresponding in position to the sensor leads 205, 205a and thereby possible to prevent the occurrence of cracks in the sensor element 10, 10a.

Third Modification

Furthermore, the rear end portion 204W, 204Wa of the sensor electrode 204, 204a is smaller in width than the front end 205Y, 205Ya of the sensor lead 205, 205a in the above embodiment as is seen in FIGS. 2 and 3A. The width relationship of the rear end portion 204W, 204Wa of the sensor electrode 204, 204a and the front end 205Y, 205Ya of the sensor lead 205, 205a is not however limited to the above and can also be set as appropriate. Alternatively, the rear end portion 204W, 204Wa of the sensor electrode 204, 204a may be the same in width as or larger in width than the front end 205Y, 205Ya of the sensor lead 205, 205a and may be the same in width than the front end portion 204Y, 204Ya of the sensor electrode 204, 204a.

Fourth Modification

Although the sensor electrode 204, 204a is generally rectangular in shape in the above embodiment, the electrode 204, 204a is not limited to such a rectangular shape and can alternatively be formed in various shapes such as polygonal shape and circular shape.

Fifth Modification

The sensor element 10, 10a is not limited to the above-embodied oxygen sensor element and is applicable in various forms for detecting a specific gas component in gas under measurement or measuring the concentration of a specific gas component in gas under measurement. For example, the sensor element 10, 10a may be designed for use in a NOx sensor.

The scope of the invention is defined with reference to the following claims.

What is claimed is:

1. A gas sensor element for detecting the concentration of a specific gas component in gas under measurement, comprising:
    a plate-shaped solid electrolyte layer extending in a longitudinal direction thereof;
    a pair of sensor electrodes arranged on a front side of the solid electrolyte layer;
    a pair of sensor leads arranged on a rear side of the solid electrolyte layer and electrically connected to the respective sensor electrode; and
    insulating layers, one of which is arranged between one of the sensor leads and the solid electrolyte layer and the other of which is arranged between the other sensor lead and the solid electrolyte layer,
    wherein the sensor electrodes have rear end portions located on the insulating layers and overlapping front end portions of the sensor leads, respectively, and
    wherein the sensor leads are denser than the sensor electrodes and have front ends located in the same positions as or positions rear of front ends of the insulating layers, respectively.

2. The gas sensor element according to claim 1, wherein the rear end portions of the sensor electrodes are located over the front end portions of the sensor leads.

3. A gas sensor comprising:
    the gas sensor element according to claim 1; and
    a housing retaining therein the gas sensor element.

* * * * *